United States Patent
Li et al.

(10) Patent No.: US 12,268,702 B2
(45) Date of Patent: Apr. 8, 2025

(54) ANTITUMOR PHARMACEUTICAL COMPOSITION COMPRISING AZVUDINE AND CHEMOTHERAPEUTIC AGENT

(71) Applicant: HENAN GENUINE BIOTECH CO., LTD., Pingdingshan (CN)

(72) Inventors: Pan Li, Pingdingshan (CN); Limin Jia, Pingdingshan (CN); Zhiyong Qin, Pingdingshan (CN); Zhaoyang Wang, Pingdingshan (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 0 days.

(21) Appl. No.: 18/200,000

(22) Filed: May 22, 2023

(65) Prior Publication Data

US 2024/0293438 A1    Sep. 5, 2024

(30) Foreign Application Priority Data

Mar. 3, 2023 (CN) .......................... 202310201602.2

(51) Int. Cl.
| | | |
|---|---|---|
| *A61K 31/7068* | (2006.01) | |
| *A61K 31/337* | (2006.01) | |
| *A61K 31/655* | (2006.01) | |
| *A61K 31/675* | (2006.01) | |
| *A61K 39/395* | (2006.01) | |
| *A61P 35/00* | (2006.01) | |
| *A61P 35/02* | (2006.01) | |

(52) U.S. Cl.
CPC ........ *A61K 31/7068* (2013.01); *A61K 31/337* (2013.01); *A61K 31/655* (2013.01); *A61K 31/675* (2013.01); *A61K 39/3955* (2013.01); *A61P 35/00* (2018.01); *A61P 35/02* (2018.01)

(58) Field of Classification Search
CPC ................................................ A61K 31/7068
USPC ........................................................ 424/133.1
See application file for complete search history.

(56) References Cited

U.S. PATENT DOCUMENTS 6,147,060 A * 11/2000 Zasloff .................... A61P 35/00
514/110

FOREIGN PATENT DOCUMENTS

| CN | 102000103 A | 4/2011 |
|---|---|---|
| WO | WO 2021/209740 A1 * | 10/2021 |

OTHER PUBLICATIONS

Wang et al (Biochemical Pharmacology, 2011, 81: 848-855).*
Jing et al (Genes & Genomics, 2022, 44: 123-131).*
Folkman (Nature Medicine, vol. 1, pp. 27-31, 1995).*
Van Cutsem et al (Journal of Clinical Oncology, 2012, 30(17): 2119-2127).*
Reck et al (Journal of Clinical Oncology, 2009, 27(8): 1227-1234).*
Guo et al (J Mater Chem, 2016, 4: 2338-2350).*
Tang et al (RSC Adv, 2018, 8: 380-389).*
Younes et al (British Journal of Haematology, 1997, 96: 328-332).*
Zhang et al (Plos One, 2017, 12(3), e0174112, 17 pages).*
Extended European Search Report issued in European Patent Application No. 23174495.4, dated Oct. 20, 2023.
Fayzullina, D. et al., "FNC: An Advanced Anticancer Therapeutic or Just an Underdog?," *Frontiers in Oncology*, 12.820647 (2022): 1-8.
Wang, F. et al., "Role of capecitabine in treating metastatic colorectal cancer in Chinese patients," *Onco Targets and Therapy*, 7 (2014): 501-511.

* cited by examiner

*Primary Examiner* — Sean E Aeder
(74) *Attorney, Agent, or Firm* — Parker Highlander PLLC

(57) ABSTRACT

The present invention discloses a pharmaceutical composition comprising azvudine and a chemotherapeutic agent. The pharmaceutical composition of the present invention shows a good synergistic effect in antitumor, and can reduce the dosage of chemotherapeutic agent, and improve the therapeutic effect and safety, thereby achieving the goal of prolonging the survival of patients.

3 Claims, 4 Drawing Sheets

ANTITUMOR PHARMACEUTICAL COMPOSITION COMPRISING AZVUDINE AND CHEMOTHERAPEUTIC AGENT

CROSS REFERENCE TO RELATED APPLICATIONS

This application claims the priority of Chinese Patent Application No. 202310201602.2, filed with the China National Intellectual Property Administration on Mar. 3, 2023, and titled with "ANTITUMOR PHARMACEUTICAL COMPOSITION COMPRISING AZVUDINE AND CHEMOTHERAPEUTIC AGENT", which is hereby incorporated by reference in its entirety.

FIELD

The present invention belongs to the field of medicines, and in particular to an antitumor pharmaceutical composition comprising azvudine.

BACKGROUND

Deoxycytidine kinase (DCK) is as an enzyme with broad substrate specificity, which can phosphorylate pyrimidine and purine deoxynucleosides, and is a key enzyme in the remedial pathway of deoxynucleotide biosynthesis. It is capable of maintaining normal DNA metabolism and phosphorylating a variety of antiviral and anticancer nucleoside analog drugs, which can only be activated after phosphorylation, thereby inhibiting tumor growth. In the past decades, apoptosis has been widely studied, and radiotherapy strategies targeting apoptosis have become one of the important means of tumor treatment.

Azvudine is a broad-spectrum RNA virus inhibitor. As a synthetic nucleoside analog of viral RNA-dependent RNA polymerase (RdRp), it is metabolized in cells into 5'-triphosphate metabolite (azvudine triphosphate) with antiviral activity, which can specifically act on the novel coronavirus polymerase (RdRp). It targets virus RdRp, and can block the synthesis and replication of RNA chain by inhibiting the activity of RdRp in the host cell. In July 2021, azvudine tablet was approved for marketing in China for the treatment of HIV-1 infected adult patients with high viral load. In July 2022, azvudine was approved for the treatment of novel coronavirus infection.

Patent document CN201010506595.X discloses use of azvudine in the treatment of tumors, such as colon cancer, liver cancer, gastric cancer, esophageal cancer, lung cancer, breast cancer, cervical cancer, leukemia, and lymphoma. It has been found that azvudine has significant inhibitory effect on various human cancer cells and transplanted tumors in animals.

Among the traditional tumor treatment methods, chemotherapy has become the most widely used clinical tumor treatment method due to its strong therapeutic effect and high drug efficacy. However, most of the chemotherapeutic drugs currently used clinically have poor selectivity, which may cause great damage to normal tissues of the human body while treating tumor tissues, thereby leading to serious toxic and side effects.

Single drug therapy has defects such as poor physical and chemical properties, low bioavailability, and poor therapeutic effect. If chemotherapeutic drugs can be combined with azvudine, the anti-tumor effect can be improved. Based on the complementary synergy between the anti-tumor mechanisms of the two drugs, synergistic enhancement of anti-tumor efficacy with chemotherapy and immunity can be achieved by double-targeting tumor cells.

SUMMARY

The present disclosure provides a pharmaceutical composition comprising azvudine (FNC) and a chemotherapeutic agent, and use of the pharmaceutical composition in the manufacture of a medicament for preventing or treating a tumor disease.

Compared with each single drug, the pharmaceutical composition of the present invention has the following advantages:
1. The combined administration improves the tumor-inhibiting effect of each single drug;
2. The occurrence of drug resistance is delayed, and the efficacy and safety are improved, thereby achieving the goal of prolonging the survival of patients.

In order to solve the technical problem of the present invention, the present invention provides a pharmaceutical composition, comprising:
   (i) azvudine or a pharmaceutically acceptable salt, a stereoisomer or an isotopic derivative thereof;
   (ii) a chemotherapeutic agent.

In a preferred embodiment of the present invention, the chemotherapeutic agent is selected from the group consisting of capecitabine, carboplatin, carmustine, chlorambucil, cisplatin, cladribine, clofazimine, cyclophosphamide, cytarabine, dacarbazine, actinomycin D, daunorubicin, paclitaxel, docetaxel, doxorubicin, epirubicin, etoposide, fludarabine, fluorouracil, gemcitabine, hydroxyurea, idarubicin, ifosfamide, irinotecan, folinic acid, doxorubicin liposome, daunorubicin liposome, lomustine, melphalan, mercaptopurine, mesna, methotrexate, mitomycin, mitoxantrone, oxaliplatin, paliittazine, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, and a combination thereof.

In a preferred embodiment of the present invention, the chemotherapeutic agent is selected from the group consisting of capecitabine, cyclophosphamide, dacarbazine, paclitaxel and a combination thereof.

In addition, the present invention further provides another pharmaceutical composition, comprising:
   (iii) azvudine or a pharmaceutically acceptable salt, a stereoisomer or an isotopic derivative thereof;
   (iv) avastin.

In a preferred embodiment of the present invention, the (i) and (ii) are administered simultaneously, separately, or sequentially, or the (i) and (ii) exist in the same dosage form.

In a preferred embodiment of the present invention, the pharmaceutical composition is used for treating a tumor-related disease.

In a preferred embodiment of the present invention, the tumor-related disease is selected from the group consisting of breast cancer, ovarian cancer, prostate cancer, melanoma, brain tumor, esophageal cancer, gastric cancer, liver cancer, pancreatic cancer, colorectal cancer, lung cancer, kidney cancer, skin cancer, glioblastoma, neuroblastoma, sarcoma, liposarcoma, osteochondroma, bone tumor, osteosarcoma, seminoma, testicular tumor, uterine cancer, head and neck tumor, multiple myeloma, malignant lymphoma, polycythemia vera, leukemia, thyroid tumor, ureter tumor, bladder tumor, gallbladder cancer, non-small cell lung cancer, cholangiocarcinoma and choriocarcinoma.

In some embodiments, the azvudine is administered at an amount selected from 1-100 mg, and the chemotherapeutic agent is administered at an amount selected from 1-500 mg.

In some embodiments, the azvudine is administered at an amount selected from 1-100 mg, and the avastin is administered at an amount selected from 1-500 mg.

In the present disclosure, the azvudine is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg and 100 mg.

In the present disclosure, the chemotherapeutic agent is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg and 500 mg.

In some embodiments, the azvudine is administered at an amount selected from 1-100 mg, and at a frequency of once a day, twice a day or three times a day, and the chemotherapeutic agent is administered at an amount selected from 1-500 mg, and at a frequency of once a day, twice a day or three times a day.

In some embodiments, the azvudine is administered at an amount selected from 1-50 mg, and at a frequency of once a day or twice a day, and the chemotherapeutic agent is administered at an amount selected from 1-100 mg, and at a frequency of once a day.

In some embodiments, the azvudine is administered at an amount selected from 1-20 mg, and at a frequency of once a day or twice a day, and the chemotherapeutic agent is administered at an amount selected from 1-40 mg, and at a frequency of once a day.

In some embodiments, the azvudine is administered at an amount selected from 1-10 mg, and at a frequency of once a day or twice a day, and the chemotherapeutic agent is administered at an amount selected from 1-10 mg, and at a frequency of once a day.

In some embodiments, the chemotherapeutic agent is administered at an amount selected from the group consisting of 1 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg and 50 mg, and at a frequency of once a day or twice a day. The chemotherapeutic agent is administered at an amount selected from 10 mg, 20 mg, 40 mg and 60 mg, and at a frequency of once a day.

In some embodiments, the azvudine is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg and 20 mg, and at a frequency of once a day or twice a day. The azvudine is administered at an amount selected from the group consisting of 1 mg, 2 mg, 4 mg and 6 mg, and at a frequency of once a day.

In some embodiments, the chemotherapeutic agent is administered at an amount selected from the group consisting of 1 mg, 2 mg, 3 mg, 4 mg, 5 mg, 6 mg, 7 mg, 8 mg, 9 mg and 10 mg, and at a frequency of once a day or twice a day. The chemotherapeutic agent is administered at an amount selected from the group consisting of 10 mg, 20 mg, 40 mg and 60 mg, and at a frequency of once a day.

In some embodiments, the chemotherapeutic agent is administered at an amount selected from the group consisting of 1 mg, 2 mg, 4 mg, 6 mg and 8 mg, and at a frequency of once a day or twice a day. The chemotherapeutic agent is administered at an amount selected from the group consisting of 1 mg, 2.5 mg, 5 mg and 10 mg, and at a frequency of once a day.

Route of the combined administration in the present invention is selected from the group consisting of oral administration, parenteral administration and transdermal administration, wherein the parenteral administration includes but is not limited to intravenous injection, subcutaneous injection and intramuscular injection, preferably oral administration.

The present invention further provides a pharmaceutical composition comprising the above azvudine and chemotherapeutic agent and one or more pharmaceutically acceptable carriers, excipients and diluents. The pharmaceutical composition can be made into any pharmaceutically acceptable dosage form. For example, it can be formulated into a tablet, a capsule, a pill, a granule, a solution, a suspension, a syrup, an injection (including an injection solution, a sterile powder for injection and a concentrated solution for injection), a suppository, an inhalant or a spray. The pharmaceutical composition can also be made into the same dosage form, for example, the azvudine and chemotherapeutic agent can be formulated into a composite tablet, a composite capsule, a composite pill, a composite granule, a composite solution, a composite suspension, a composite syrup, a composite injection (including an injection solution, a sterile powder for injection and a concentrated solution for injection), a composite suppository, a composite inhalant or a composite spray.

The present invention further provides a method for treating a tumor disease, comprising administering an effective amount of the above azvudine and an effective amount of the above chemotherapeutic agent to a subject in need thereof.

The present invention further provides a pharmaceutical kit for use in a medicament for treating a tumor disease, which comprises the pharmaceutical composition of azvudine and chemotherapeutic agent described in the present disclosure.

In the present invention, azvudine is administered in combination with a chemotherapeutic agent, thereby enhancing the effect of drugs for treating a tumor disease.

The "combination" described in the present invention is a mode of administration that refers to the administration of at least one dose of azvudine and at least one dose of chemotherapeutic agent within a certain period of time, wherein both substances show pharmacological effects. The period of time can within one administration cycle, preferably within 4 weeks, within 3 weeks, within 2 weeks, within 1 week, or within 24 hours, more preferably within 12 hours. The azvudine and chemotherapeutic agent can be administered simultaneously or sequentially. Such a treatment that azvudine and a chemotherapeutic agent are administered by the same route of administration or by different routes of administration is included in this period of time.

DETAILED DESCRIPTION

Figure 1:
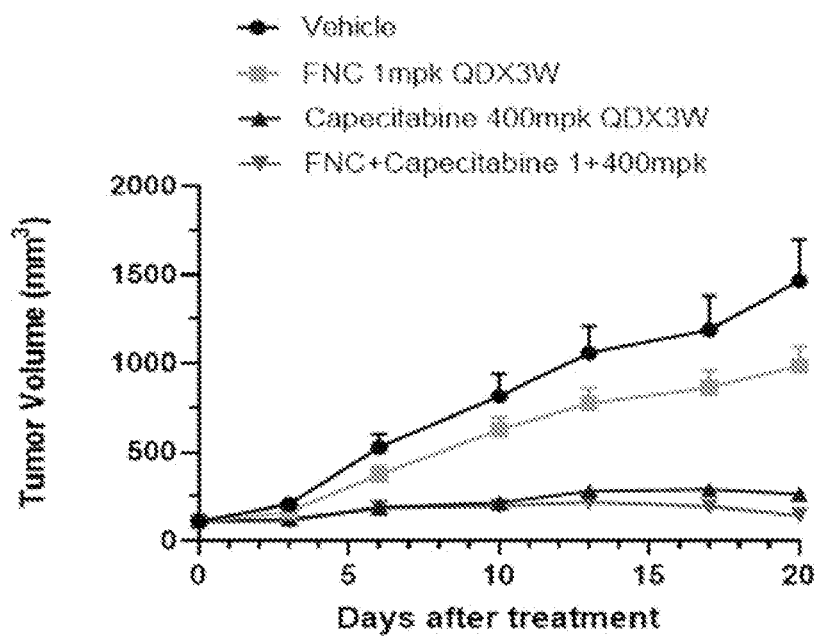
FIG. 1 shows the effects of azvudine and capecitabine used alone or in combination on the subcutaneous xenograft tumor volume in human colon cancer COLO 205 tumor model.
Figure 2:
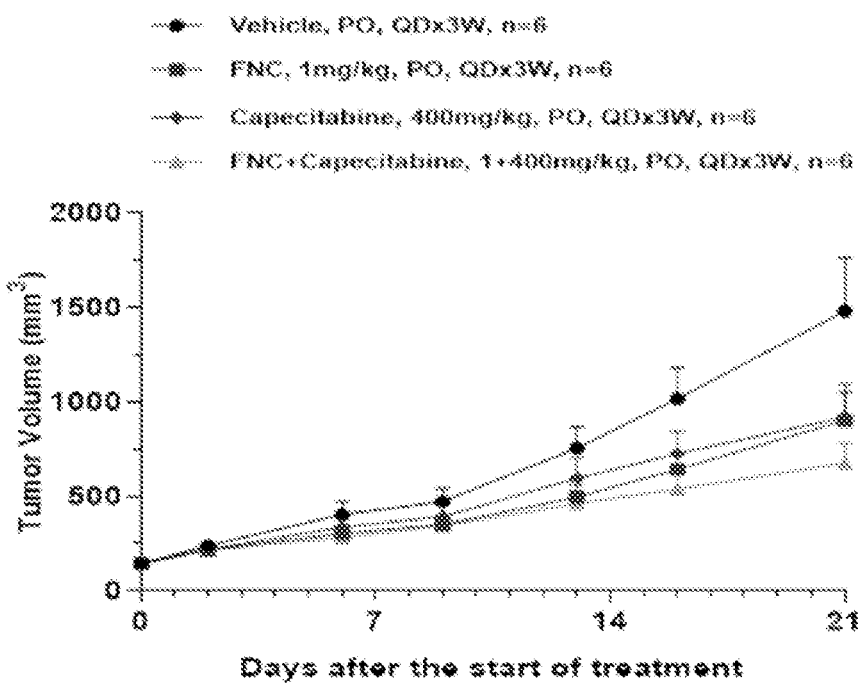
FIG. 2 shows the effects of azvudine and capecitabine used alone or in combination on the subcutaneous xenograft tumor volume in human colorectal cancer LoVo tumor model.
Figure 3:
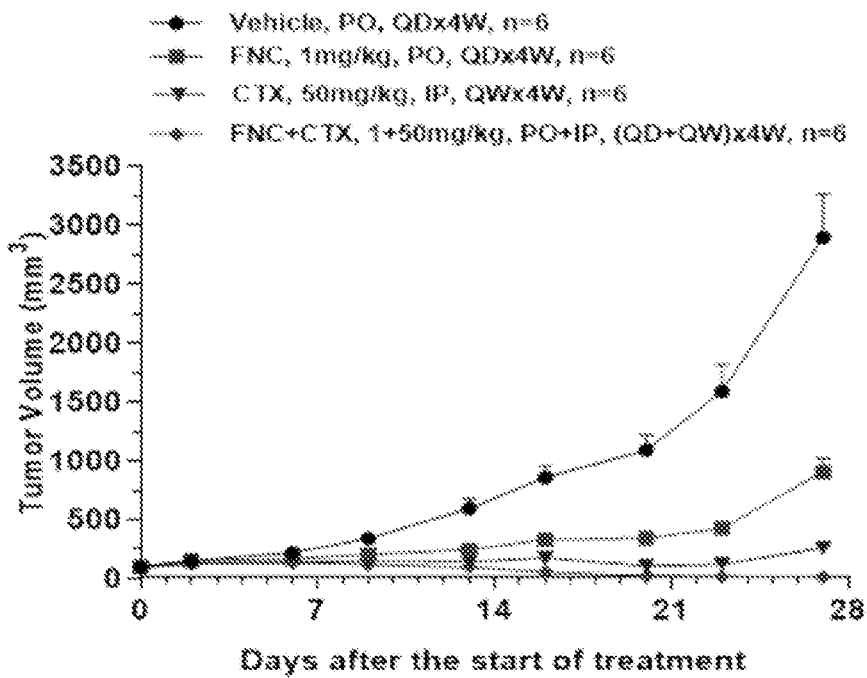
FIG. 3 shows the effects of azvudine and cyclophosphamide used alone or in combination on the subcutaneous xenograft tumor volume in human Burkitt's lymphoma cells Daudi tumor model.
Figure 4:
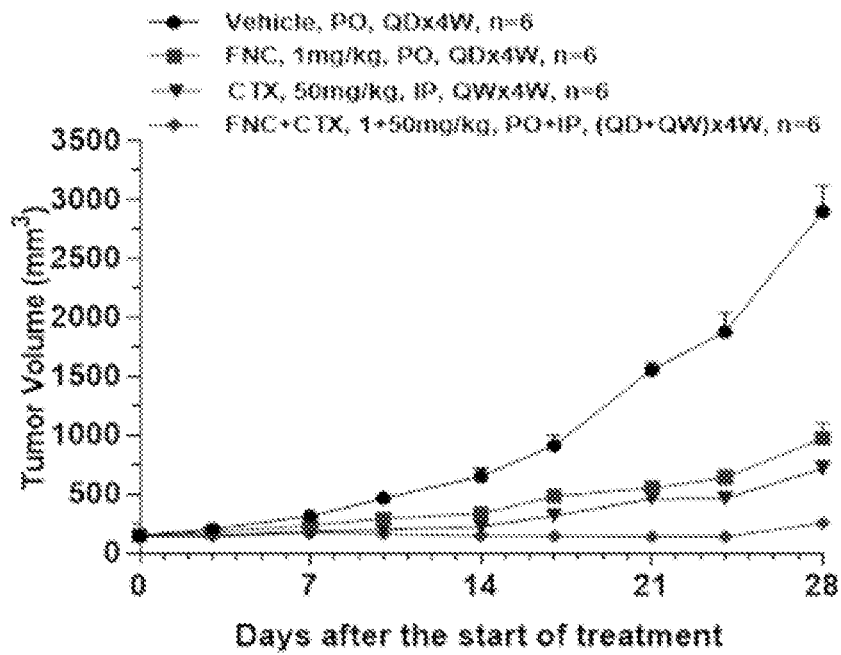
FIG. 4 shows the effects of azvudine and cyclophosphamide used alone or in combination on the subcutaneous xenograft tumor volume in human acute lymphoblastic leukemia cell MOLT4 tumor model.
Figure 5:
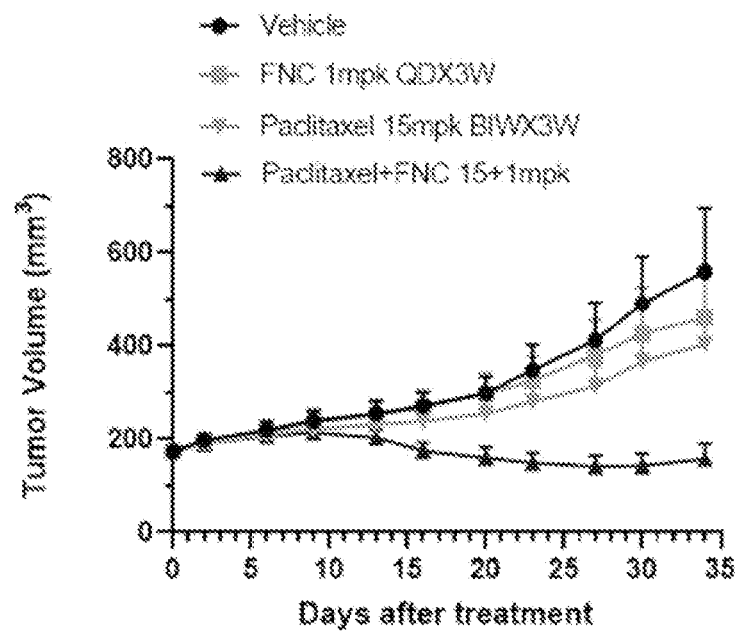
FIG. 5 shows the effects of azvudine and paclitaxel used alone or in combination on the subcutaneous xenograft tumor volume in human ovarian cancer OVCAR-8 tumor model.
Figure 6:
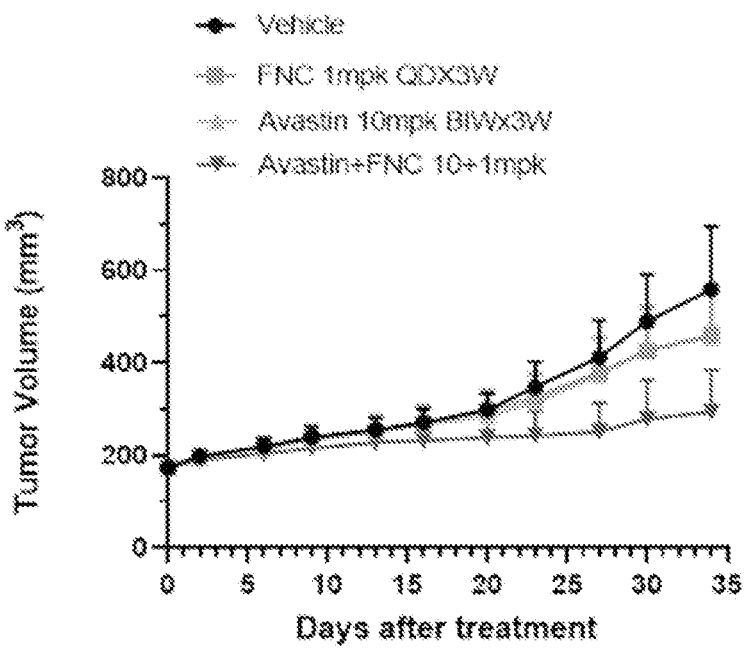
FIG. 6 shows the effects of azvudine and avastin used alone or in combination on the subcutaneous xenograft tumor volume in human ovarian cancer OVCAR-8 tumor model.
Figure 7:
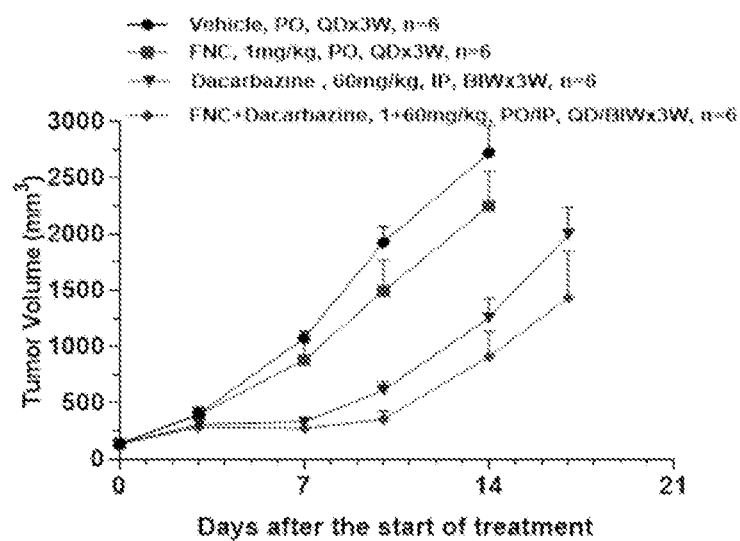
FIG. 7 shows the effects of azvudine and dacarbazine used alone or in combination on the subcutaneous xenograft tumor volume of human melanoma A2058 tumor model.

The following will describe the present disclosure in more detail in conjunction with examples, and the examples of the present disclosure are only used to illustrate the technical solutions of the present disclosure, and do not limit the essence and scope of the present disclosure.

Experimental Materials

Experimental Animals and Breeding Environment
Experimental Animals

Experimental animals were 68 (48 plus 20 spare mice) BALB/c female nude mice, 7-8 weeks old (the age of mice at the time of tumor cell inoculation) and weighing 15.7-20.7 g, which were purchased from Beijing VitalRiver Experimental Animal Technology Co., Ltd. Breeding environment was SPF grade. The experimental animals were all kept in an independent ventilated box with constant temperature and humidity. The temperature of the breeding room was 20-26° C., the humidity was 40-70%. The breeding room was ventilated 10-20 times per hour. The alternating time of day and night was 12 h/12 h. The mice were continuously supplied with cobalt 60 radiation sterilized mouse complete pellet feed, and had free access to the feed. The mice drank tap water (available after sterilization with high-pressure steam), which was continuously supplied using a water-drinking bottle, and had free access to water. The mouse box was a polysulfone mouse box, which was used after sterilization under high pressure, with a size of 325 mm×210 mm×180 mm.

Example 1 Test Results and Discussion of the Anti-Tumor Effect of Azvudine in Combination with Capecitabine on the Colo 205 Human Colon Cancer Model Cell Culture Colo 205 cells were cultured in RPMI1640 medium containing 10% fetal bovine serum. Colo 205 cells in the exponential growth phase were collected, resuspended in PBS to an appropriate concentration and mixed with Matrigel at a ratio of 1:1. The resulting mixture was used for subcutaneous inoculation of tumor in mice. $5 \times 10^6$ Colo 205 cells were subcutaneously inoculated on the right side of female mice. The day of inoculation was defined as Day 0. When the average tumor volume reached 110.26 mm$^3$, the mice were randomly divided into groups according to tumor size.

Relative tumor proliferation rate, T/C %, refers to the percentage value of the relative tumor volume or tumor weight of the treatment group and the control group at a certain time point, which was calculated as follows:

Efficacy Evaluation Criteria

T/C %=$T_{RTV}/C_{RTV} \times 100\%$ ($T_{RTV}$: the average RTV of the treatment group; $C_{RTV}$: the average RTV of the vehicle control group; RTV=$V_t/V_0$, where $V_0$ is the tumor volume of the animal when grouped, and $V_t$ is the tumor volume of the animal after treatment);

or T/C %=$T_{TW}/C_{TW} \times 100\%$ ($T_{TW}$: the average tumor weight of the treatment group at the end of the experiment; $C_{TW}$: the average tumor weight of the vehicle control group at the end of the experiment).

Relative tumor inhibition rate, TGI (%), was calculated according to the formula as follows: TGI %=(1−T/C)× 100%. (T and C are the relative tumor volumes (RTV) or tumor weights (TW) of the treatment group and the control group at a specific time point).

On the 25$^{th}$ day after tumor inoculation (on the 20$^{th}$ day after grouping), the mice in the vehicle group had an average tumor volume of 1465.47 mm$^3$, and the single drug azvudine 1 mg/kg treatment group had an average tumor volume of 985.14 mm$^3$, which had no statistically significant difference compared with the control group (p=0.540), with a relative tumor inhibition rate TGI (%) of 32.43%. The capecitabine 400 mg/kg treatment group had an average tumor volume of 264.96 mm$^3$, which had statistically significant difference compared with the control group (p<0.001), with a relative tumor inhibition rate TGI (%) of 81.93%. The combination group of azvudine 1 mg/kg and capecitabine 400 mg/kg had an average tumor volume of 144.76 mm$^3$, which had statistically significant difference compared with the control group (p<0.001), with a relative tumor inhibition rate TGI (%) of 90.14%.

TABLE 1

Experimental design of antitumor effect of test drugs with different doses on COLO 205 human colon cancer tumor model

| Group | Dose (mg/kg) | Administration route | Administration cycle |
|---|---|---|---|
| Blank group | — | p.o. | QD × 3 weeks |
| Azvudine | 1 | p.o. | QD × 3 weeks |
| Capecitabine | 400 | p.o. | QD × 3 weeks |
| Azvudine + Capecitabine | 1 + 400 | p.o. | QD × 3 weeks |

TABLE 2

Drug efficacy analysis of each group in the Colo 205 human colon cancer model

| | On the 25$^{th}$ day after inoculation (on the 20$^{th}$ day after grouping)$^a$ | | | |
|---|---|---|---|---|
| Test drug | Tumor volume | TGI(%) | T/C(%) | P$^b$ |
| Vehicle | 1465.47 ± 233.57(6) | — | — | — |
| Azvudine (1 mpk) | 985.14 ± 108.58(6) | 32.43 | 67.57 | 0.540 |
| Capecitabine (400 mpk) | 264.96 ± 38.65(6) | 81.93 | 18.07 | <0.001 |
| Azvudine + Capecitabine (1 + 400 mpk) | 143.76 ± 23.45(6) | 90.14 | 9.86 | <0.001 |

Results of Tumor Weight Suppression

TABLE 3

Tumor weight analysis of each group in the Colo 205 human colon cancer model

| Test drug | Tumor weight (mg) | TGI | T/C (%) | P (compared to the control group) |
|---|---|---|---|---|
| Vehicle | 1373.15 ± 200.04(6) | — | — | — |
| Azvudine (1 mpk) | 986.10 ± 107.78(6) | 71.81 | 28.19 | 0.926 |
| Capecitabine (400 mpk) | 193.35 ± 28.54(6) | 14.08 | 85.92 | <0.001 |
| Azvudine + Capecitabine (1 + 400 mpk) | 98.80 ± 20.27(6) | 7.2 | 92.8 | <0.001 |

Example 2 Pharmacodynamic Study of Azvudine in Combination with Capecitabine in Human Colon Cancer LoVo Cells Cell Culture Human colon cancer cells LoVo (Cat. No.: ECACC-87060101) were cultured in vitro as a monolayer in F12K medium containing 10% fetal bovine serum, 100 U/mL penicillin and 100 μg/mL streptomycin, in a 37° C. and 5% $CO_2$ incubator. The cells were routinely digested with trypsin-EDTA and passaged twice a week. When the cell saturation reached 80%-90% and the cell number achieved the requirement, the cells were collected, counted and inoculated.

0.1 mL)(10×10$^6$) of LoVo cells were subcutaneously inoculated on the right back of each mouse. The grouping administration was started when the average tumor volume reached about 147 mm$^3$.

TABLE 4

Experimental design of antitumor effect of test drugs with different doses on COLO 205 human colon cancer tumor model

| Group | Dose (mg/kg) | Administration route | Administration cycle |
|---|---|---|---|
| Blank group | — | p.o. | QD × 3 weeks |
| Azvudine | 1 | p.o. | QD × 3 weeks |
| Capecitabine | 400 | p.o. | QD × 3 weeks |
| Azvudine + Capecitabine | 1 + 400 | p.o. | QD × 3 weeks |

Experimental Results

The tumor volume changes and the tumor weight changes in each group (on the 21$^{st}$ day of administration) after administration of test drugs for treating BALB/c nude mice with Lovo cell subcutaneous xenograft tumor are shown in Table 5 and Table 6 respectively.

TABLE 5

Evaluation of the antitumor effect of test drugs on the LoVo xenograft tumor model (calculated based on the tumor volume on the 21$^{st}$ day of administration)

| | On the 21$^{st}$ day of administration | | | |
|---|---|---|---|---|
| Test drug | Tumor volume (mm$^3$) | T/C (%) | TGI (%) | P (%) |
| Vehicle | 1481 ± 311 | — | — | — |
| Azvudine (1 mpk) | 902 ± 163 | 62.00 | 43.40 | 0.635 |
| Capecitabine (400 mpk) | 919 ± 190 | 60.94 | 42.11 | 0.696 |
| Azvudine + Capecitabine (1 + 400 mpk) | 676 ± 115 | 48.18 | 60.29 | 0.282 |

TABLE 6

Evaluation of the antitumor effect of test drugs on the LoVo xenograft tumor model (calculated based on the tumor weight on the 21$^{st}$ day of administration)

| | On the 21$^{st}$ day of administration | | |
|---|---|---|---|
| Test drug | Tumor weight (g) | T/C (%) | P (%) |
| Vehicle | 1.411 ± 0.304 | — | — |
| Azvudine (1 mpk) | 0.937 ± 0.142 | 66.37 | 0.827 |
| Capecitabine (400 mpk) | 0.893 ± 0.173 | 63.27 | 0.799 |
| Azvudine + Capecitabine (1 + 400 mpk) | 0.643 ± 0.091 | 45.56 | 0.368 |

In this experiment, the in vivo efficacy of the test drugs in the LoVo xenograft tumor model was evaluated. The tumor volume and tumor weight of each group on the 21$^{st}$ day of administration are shown in Table 5, Table 6 and Table 2, respectively. On the 21$^{th}$ day after the start of administration, the tumor volume of the tumor-bearing mice in the blank control group reached 1481 mm$^3$. Compared with the blank control group, the test drug azvudine (1 mg/kg) group showed a small tumor inhibitory effect, with a tumor volume of 902 mm$^3$, T/C of 62.00%, TGI of 43.40%, and p-value of 0.086. Compared with the blank control group, the test drug capecitabine (400 mg/kg) group showed a small tumor inhibitory effect, with a tumor volume of 919 mm$^3$, T/C of 60.94%, TGI of 42.11%, and p value of 0.696.

Compared with the blank control group, the test drugs combination group of azvudine+capecitabine (1+400 mg/kg) showed a significant tumor inhibitory effect, with a tumor volume of 676 mm$^3$, T/C of 48.18%, TGI of 60.29% and p-value of 0.282. The combined administration of azvudine+capecitabine can improve the antitumor effect of single drug capecitabine in the LoVo colorectal tumor, and can increase TGI from 42.1% to 60.3%.

Example 3 In Vivo Pharmacodynamics of Azvudine in Combination with Cyclophosphamide on Human Burkitt's Lymphoma Cell Daudi Subcutaneous Xenograft Tumor Model Human Burkitt's lymphoma cells Daudi (Cat. No.: DSMZ-ACC129) were in vitro suspended and cultured in RPMI 1640 medium containing 10% fetal bovine serum, 2 mM glutamine, 100 U/mL penicillin and 100 μg/mL streptomycin, in a 37° C. and 5% $CO_2$ incubator. When the cell saturation achieved 80%-90% and the cell number reached the requirement, the cells were collected, counted and inoculated.

Tumor Cell Inoculation 0.2 mL (10×10$^6$) of Daudi cells (added with Matrigel at a volume ratio of 1:1) were subcutaneously inoculated on the right back of each mouse. The grouping administration was started when the average tumor volume reached about 100 mm$^3$.

| Group | Dose (mg/kg) | Administration route | Administration cycle |
|---|---|---|---|
| Blank group | — | p.o. | QD × 4 weeks |
| Azvudine | 1 | p.o. | QD × 4 weeks |
| Cyclophosphamide | 50 | i.p. | QD × 4 weeks |
| Azvudine + Cyclophosphamide | 1 + 50 | p.o. + i.p. | QD × 4 weeks |

Experimental Results

The changes of tumor volume and tumor weight in each group after administration of test drugs for treating CB 17 SCID mice with Daudi cell subcutaneous xenograft tumor are shown in Table 8 and Table 9 respectively.

TABLE 8

Tumor volume on the 27$^{th}$ day of administration

| Treatment | Tumor volume (mm$^3$) on the 27$^{th}$ day | T/C (%) | TGI (%) | p value (%) |
|---|---|---|---|---|
| Vehicle | 2,895 ± 403 | — | — | — |
| Azvudine(1 mg/kg) | 909 ± 120 | 30.64 | 71.09 | <0.0001 |
| Cyclophosphamide (50 mg/kg) | 263 ± 54 | 8.83 | 94.17 | <0.0001 |
| Azvudine + Cyclophosphamide (1 + 50 mg/kg) | 13 ± 3 | 0.42 | 103.15 | <0.0001 |

TABLE 9

Tumor weight on the 27$^{th}$ day of administration

| Group | Tumor weight (g) (On the 27$^{th}$ day) | T/C$_{weight}$ (%) | p value$^c$ |
|---|---|---|---|
| Vehicle | 2.984 ± 0.439 | — | — |
| Azvudine (1 mg/kg) | 0.996 ± 0.143 | 33.38 | <0.0001 |
| Cyclophosphamide (50 mg/kg) | 0.343 ± 0.066 | 11.49 | <0.0001 |
| Azvudine + Cyclophosphamide (1 + 50 mg/kg) | 0.019 ± 0.004 | 0.62 | <0.0001 |

In this experiment, the in vivo efficacy of the test drugs in the Daudi xenograft tumor model was evaluated. The tumor volumes of each group at different time points are shown in Table 8 and Table 9. On the 27$^{th}$ day after the start of administration, the tumor volume of the tumor-bearing mice in the blank control group reached 2,895 mm$^3$. Compared with the blank control group, the test drug azvudine (1 mg/kg) group showed a significant tumor inhibitory effect, with a tumor volume of 909 mm$^3$, T/C of 30.64%, TGI of 71.09% and p-value of <0.0001. Compared with the blank control group, the test drug cyclophosphamide (50 mg/kg) showed a significant tumor inhibitory effect, with a tumor volume of 263 mm$^3$, T/C of 8.83%, TGI of 94.17% and p value of <0.0001. Compared with the blank control group, the test drugs combination group of azvudine+cyclophosphamide (1+50 mg/kg) showed a significant tumor inhibitory effect, with a tumor volume of 13 mm$^3$, T/C of 0.42%, TGI of 103.15%, and p-value of <0.0001.

In this experiment, the test drugs azvudine (1 mg/kg) in combination with cyclophosphamide can improve the tumor inhibitory effect of single drug CTX in the human Burkitt's lymphoma cell Daudi, and increase TGI from 94.17% to 103.15%.

Example 4 In Vivo Pharmacodynamic Study of Azvudine in Combination with Cyclophosphamide on Human Acute Lymphoblastic Leukemia Cell MOLT4 Cell Subcutaneous Xenograft Tumor Model Cell Culture Human acute lymphoblastic leukemia cells MOLT4 (Cat. No.: ECACC-85011413) were in vitro suspended and cultured in RPMI 1640 medium containing 10% fetal bovine serum, 100 U/mL penicillin and 100 μg/mL streptomycin, in a 37° C. and 5% $CO_2$ incubator. When the cell saturation achieved 80%-90% and the cell number reached the requirement, the cells were collected, counted and inoculated.

Tumor Cell Inoculation 0.2 mL (10×10$^6$) of MOLT4 cells (added with Matrigel at a volume ratio of 1:1) were subcutaneously inoculated on the right back of each mouse. The grouping administration was started when the average tumor volume reached about 148 mm$^3$.

| Group | Dose (mg/kg) | Administration route | Administration cycle |
|---|---|---|---|
| Blank group | — | p.o. | QD × 4 weeks |
| Azvudine | 1 | p.o. | QD × 4 weeks |
| Cyclophosphamide | 50 | i.p. | QD × 4 weeks |
| Azvudine + Cyclophosphamide | 1 + 50 | p.o. + i.p. | QD × 4 weeks |

The changes of tumor volume and tumor weight in each group after administration of test drugs for treating SCID Beige mice with MOLT4 cell subcutaneous xenograft tumor are shown in Table 10 and Table 11.

TABLE 10

Tumor volume on the 28$^{th}$ day of administration

| Treatment | Tumor volume (mm$^3$) on the 28$^{th}$ day | T/C (%) | TGI (%) | p value |
|---|---|---|---|---|
| Vehicle | 2,896 ± 247 | — | — | — |
| Azvudine(2 mg/kg) | 986 ± 179 | 33.55 | 69.49 | <0.0001 |
| Cyclophosphamide (50 mg/kg) | 716 ± 76 | 24.53 | 79.34 | <0.0001 |
| Azvudine + Cyclophosphamide (1 + 50 mg/kg) | 253 ± 36 | 8.75 | 96.14 | <0.0001 |

TABLE 11

Tumor weight on the 28$^{th}$ day of administration

| Group | Tumor weight (g) (On the 28$^{th}$ day) | T/C$_{weight}$ (%) | p value |
|---|---|---|---|
| Vehicle | 2.971 ± 0.228 | — | — |
| Azvudine (1 mg/kg) | 1.168 ± 0.145 | 39.31 | <0.0001 |
| Cyclophosphamide (50 mg/kg) | 0.822 ± 0.065 | 27.65 | <0.0001 |
| Azvudine + Cyclophosphamide (1 + 50 mg/kg) | 0.344 ± 0.050 | 11.56 | <0.0001 |

In this experiment, the in vivo efficacy of the test drugs in the MOLT4 xenograft tumor model was evaluated. The tumor volumes of each group at different time points are shown in Table 10 and Table 11. On the 28$^{th}$ day after the start of administration, the tumor volume of the tumor-bearing mice in the blank control group reached 2,896 mm$^3$. Compared with the blank control group, the test drug azvudine (1 mg/kg) group showed a tumor inhibitory effect, with a tumor volume of 979 mm$^3$, T/C of 33.89, TGI of 69.73%, and p-value of <0.0001. Compared with the blank control group, cyclophosphamide CTX (50 mg/kg) group showed a significant tumor inhibitory effect, with a tumor volume of 716 mm$^3$, T/C of 24.53%, TGI of 79.34%, and p value of <0.0001. Compared with the blank control group, the test drugs combination group of azvudine+cyclophosphamide (1+50 mg/kg) showed a significant tumor inhibitory effect, with a tumor volume of 253 mm$^3$, T/C of 8.75%, TGI of 96.14%, and p-value of <0.001. The analysis and statistical results of the tumor weight in the test drugs combination group were basically consistent with the tumor volume data.

In this experiment, the test drugs azvudine (1 mg/kg), cyclophosphamide (50 mg/kg) and azvudine+cyclophosphamide (1+50 mg/kg) under test doses had significant inhibitory effect on the growth of MOLT4 xenograft tumor. In this experiment, the test substances azvudine (1 mg/kg) in combination with cyclophosphamide can improve the tumor inhibitory effect of single drug cyclophosphamide in MOLT4 human acute lymphoblastic leukemia tumor, and increase TGI from 79.34% to 96.14%.

Example 5 Efficacy Evaluation of Azvudine in Combination with Paclitaxel in Human Ovarian Cancer OVCAR-8 Tumor Model OVCAR-8 cells were cultured in RPMI1640 medium containing 10% fetal bovine serum. OVCAR-8 cells in the exponential growth phase were collected, resuspended in PBS to an appropriate concentration and mixed with Matrigel at a ratio of 1:1. The resulting mixture was used for subcutaneous inoculation of tumor in mice.

1×10$^7$ OVCAR-8 cells were inoculated subcutaneously on the right side of female mice. When the average tumor volume achieved 174.25 mm$^3$, the mice were randomly divided into groups according to tumor size.

The experimental protocols for animal experiments in this experiment were reviewed and approved by the CrownBio IACUC committee. During the experiment, the animal experiments were performed in accordance with the requirements of AAALAC. After tumor inoculation was completed, the impact of tumor growth and treatment on normal behavior of animals was routinely monitored, specifically the activity of experimental animals, food intake and water intake, body weight gain or loss (body weight was measured twice a week), eye, hair and other abnormalities. The clinical symptoms observed during the experiment were recorded in the original data. The tumor volume was calculated according to the following formula: tumor volume (mm$^3$)=½×(a× b$^2$) (where a represents long diameter and b represents short diameter).

Relative tumor proliferation rate, T/C %, refers to the percentage value of the relative tumor volume or tumor weight of the treatment group and the control group at a certain time point, which was calculated as follows:

T/C %=T$_{RTV}$/C$_{RTV}$×100% (T$_{RTV}$: the average RTV of the treatment group; C$_{RTV}$: the average RTV of the vehicle control group; RTV=V$_t$/V$_0$, where V$_0$ is the tumor volume of the animal when grouped, and V$_t$ is the tumor volume of the animal after treatment);

or T/C %=T$_{TW}$/C$_{TW}$×100% (T$_{TW}$: the average tumor weight of the treatment group at the end of the experiment; C$_{TW}$: the average tumor weight of the vehicle control group at the end of the experiment).

Relative tumor inhibition rate, TGI (%), was calculated according to the formula as follows: TGI %=(1−T/C)× 100%. (T and C are the relative tumor volumes (RTV) or tumor weights (TW) of the treatment group and the control group at a specific time point).

To compare tumor volumes of different treatment groups on a given day, first the assumption of homogeneity of variance among all groups was tested using the Bartlett test. When the p-value of Bartlett's test was not less than 0.05, whether all group means were equal was tested using one-way ANOVA. If the p-value of the one-way ANOVA was less than 0.05, pairwise comparisons among all groups were conducted using Tukey's HSD test, or pairwise comparisons between each treatment group and control group were conducted using Dunnett's t-test. When the p-value of Bartlett's test was less than 0.05, whether the medians of all groups were equal was tested using Kruskal Wallis test. If the p-value of the Kruskal Wallis test was less than 0.05, pairwise comparisons among all groups or between each treatment group and control group were conducted using Conover test, and the corresponding p-value correction was performed according to the number of groups in the multiple test.

In addition, for the purpose of exploratory data analysis, pairwise comparisons among all groups at any time point were performed. Since this comparison was only directed to tumor volume data of two test groups at specific time points, no multiple test correction was required. First, the assumption of homogeneity of variance between two groups was verified using Bartlett test. When the p value of the Bartlett test was not less than 0.05, whether the means of two groups were equal was tested using Welch's t test. When the p value of the Bartlett test was less than 0.05, whether the medians of two groups were equal was tested using Mann Whitney U test.

All statistical analysis and graphing were performed in the R language environment (version 3.3.1). Unless otherwise specified, all tests were two-tailed tests, and p value less than 0.05 was considered statistically significant.

Experimental Results

On the 34$^{th}$ day of administration, the tumor volume of the vehicle control group was 558.68 mm$^3$. The average tumor volumes of the test drug azvudine 1 mg/kg treatment group, the positive drug paclitaxel 15 mg/kg treatment group, and the positive drug avastin 10 mg/kg treatment group were 460.67 mm$^3$, 403.40 mm$^3$, and 456.04 mm$^3$ respectively, which showed no statistically significant difference compared with the control group (p=0.952, 0.769, and 0.957), with relative tumor inhibition rates TGI (%) of 18.09%, 26.49%, and 17.70%, respectively. The average tumor volume of the combination treatment group of test drugs azvudine 1 mg/kg and paclitaxel 15 mg/kg was 157.34 mm$^3$, which was statistically significantly different from the control group (p=0.00707), with a relative tumor inhibition rate TGI (%) of 71.57%. The combined administration of the test drugs azvudine and paclitaxel significantly improved the anti-tumor effect of single drug paclitaxel (with a TGI of 26.5%). The average tumor volume of the combination treatment group of test drugs azvudine 1 mg/kg and avastin 10 mg/kg was 294.36 mm$^3$, which was statistically significantly different from that of the control group (p=0.140), with a relative tumor inhibition rate TGI (%) of 48.61%. The combined administration of test drugs azvudine and avastin significantly improved the antitumor effect of single drug avastin (with a TGI of 17.70%). The tumor growth of each treatment group and control group is shown in Table 12.

TABLE 12

Drug efficacy analysis of each group of azvudine in combination with paclitaxel or avastin in the OVCAR-8 human ovarian cancer model

| Experimental group | Tumor volume ($\bar{x} \pm S$) | TGI (%) | T/C (%) | P Value (compared with control group) |
|---|---|---|---|---|
| The first group Vehicle | 558.68 ± 136.75(6) | — | — | — |
| The second group Azvudine 1 mg/kg | 460.67 ± 105.37(6) | 18.09 | 81.91 | 0.952 |
| The third group Paclitaxel 15 mg/kg | 403.40 ± 69.43(6) | 26.49 | 73.51 | 0.769 |
| The fourth group Azvudine + Paclitaxel 1 + 15 mg/kg | 157.34 ± 33.68(6) | 71.57 | 28.43 | 0.00707 |
| The fifth group Avastin 10 mg/kg | 456.04 ± 110.65(6) | 17.70 | 82.30 | 0.957 |
| The sixth group Azvudine + Avastin 1 + 10 mg/kg | 294.36 ± 90.69(6) | 48.61 | 51.39 | 0.140 |

Example 6 In Vivo Pharmacodynamic Study of Azvudine in Combination with Dacarbazine on Human Melanoma A2058 Cell Subcutaneous Xenograft Tumor Model Human melanoma cells A2058 (Cat. No.: CRL-11147) were cultured in vitro as a monolayer in DMEM medium containing 10% fetal bovine serum, 100 U/mL penicillin and 100 μg/mL streptomycin, in a 37° C. and 5% $CO_2$ incubator. The cells were routinely digested with trypsin-EDTA and passaged twice a week. When the cell saturation reached 80%-90% and the cell number achieved the requirement, the cells were collected, counted and inoculated.

Tumor Cell Inoculation 0.2 mL (5×10$^6$) of A2058 cells were added with Matrigel, and the mixture was subcutaneously inoculated on the right back of each mouse. The grouping administration was started when the average tumor volume reached about 136 mm$^3$.

Analysis of Results

TABLE 13

Evaluation of antitumor efficacy of azvudine in combination with dacarbazine on A2058 xenograft tumor model (calculated based on the tumor volume on the 14$^{th}$ day of administration)

| Treatment | Tumor volume (mm$^3$)$^a$ on the 14$^{th}$ day | T/C (%) | TGI$^b$ (%) | p value (%) |
|---|---|---|---|---|
| Vehicle | 2,724 ± 259 | — | — | — |
| Azvudine (1 mg/kg) | 2.253 ± 335 | 79.67 | 18.22 | 0.518 |
| Dacarbazine (60 mg/kg) | 1,255 ± 186 | 44.77 | 56.74 | 0.002 |
| Azvudine + Dacarbazine (1 + 60 mg/kg) | 910 ± 247 | 31.52 | 70.07 | <0.001 |

In this example, the in vivo efficacy of the test drugs in the A2058 xenograft tumor model was evaluated. The tumor volumes of each group at different time points are shown in Table 13. On the 14$^{th}$ day after the start of administration, the tumor volume of the tumor-bearing mice in the blank control group reached 2724 mm$^3$. Compared with the blank control group, the test drug azvudine (1 mg/kg) group showed a small tumor inhibitory effect, with a tumor volume of 2253 mm$^3$, T/C of 79.67%, TGI of 18.22%, and p value of 0.518. Compared with the blank control group, dacarbazine (60 mg/kg) had a tumor inhibitory effect, with a tumor volume of 1255 mm$^3$, T/C of 44.77%, TGI of 56.74%, and p value of 0.002. Compared with the blank control group, the test drugs combination group of azvudine+dacarbazine (1+60 mg/kg) showed a significant tumor inhibitory effect, with a tumor volume of 910 mm$^3$, T/C of 31.52%, TGI of 70.07%, and p-value of <0.001.

Although the specific embodiments of the present invention have been described above, those skilled in the art should understand that these are only examples, and various changes or modifications can be made to these embodiments without departing from the principle and essence of the present invention. Accordingly, the protection scope of the present invention is defined by the claims.

The invention claimed is:

1. A method for treating a tumor-related disease, comprising administering a synergistic pharmaceutical composition, comprising
   (i) azvudine or a pharmaceutically acceptable salt, a stereoisomer or an isotopic derivative thereof; and
   (ii) cyclophosphamide,
to a subject in need thereof; wherein the tumor-related disease is selected from the group consisting of malignant lymphoma, and leukemia.

2. A method for treating a tumor-related disease, comprising administering a synergistic pharmaceutical composition comprising (i) azvudine or a pharmaceutically acceptable salt, a stereoisomer or an isotopic derivative thereof, and (ii) avastin to a subject in need thereof, wherein the tumor-related disease is ovarian cancer.

3. A method for treating a tumor-related disease, comprising administering a synergistic pharmaceutical composition, comprising (i) azvudine or a pharmaceutically acceptable salt, a stereoisomer or an isotopic derivative thereof, and (ii) paclitaxel, to a subject in need thereof; wherein the tumor-related disease is ovarian cancer.

* * * * *